United States Patent
Ohishi et al.

(10) Patent No.: US 7,604,404 B2
(45) Date of Patent: Oct. 20, 2009

(54) X-RAY IMAGING APPARATUS

(75) Inventors: Satoru Ohishi, Otawara (JP); Masashi Hirose, Saitama (JP)

(73) Assignees: Kabushiki Kaisha Toshiba, Tokyo (JP); Toshiba Medical Systems Corporation, Otawara-shi (JP)

( * ) Notice: Subject to any disclaimer, the term of this patent is extended or adjusted under 35 U.S.C. 154(b) by 0 days.

(21) Appl. No.: 12/174,055

(22) Filed: Jul. 16, 2008

(65) Prior Publication Data

US 2009/0022271 A1  Jan. 22, 2009

(30) Foreign Application Priority Data

Jul. 18, 2007  (JP) .............................. 2007-187426

(51) Int. Cl.
*H05G 1/02* (2006.01)

(52) U.S. Cl. .................... 378/197; 378/98.12; 378/901; 600/431

(58) Field of Classification Search ............... 378/4–20, 378/98.12, 193–198; 600/407, 425, 431
See application file for complete search history.

(56) References Cited

U.S. PATENT DOCUMENTS 7,269,246 B2 * 9/2007 Ohishi ..................... 378/98.12
2009/0103790 A1    4/2009 Yamagishi et al.

FOREIGN PATENT DOCUMENTS

JP    2007-130244    5/2007

* cited by examiner

*Primary Examiner*—Courtney Thomas
(74) *Attorney, Agent, or Firm*—Oblon, Spivak, McClelland, Maier & Neustadt, L.L.P.

(57) ABSTRACT

An X-ray imaging apparatus includes a substantially C-arm, a support mechanism which rotatably supports substantially the C-arm, a rotation driving unit which drives rotation of substantially the C-arm, an X-ray tube mounted on substantially the C-arm, an X-ray detector mounted on substantially the C-arm, and a control unit which controls at least one of the rotation driving unit and an imaging control unit to make intervals between a plurality of contrast-enhanced images shorter than intervals between a plurality of mask images by changing a rotational speed of substantially the C-arm before and after injection of a contrast medium.

20 Claims, 4 Drawing Sheets

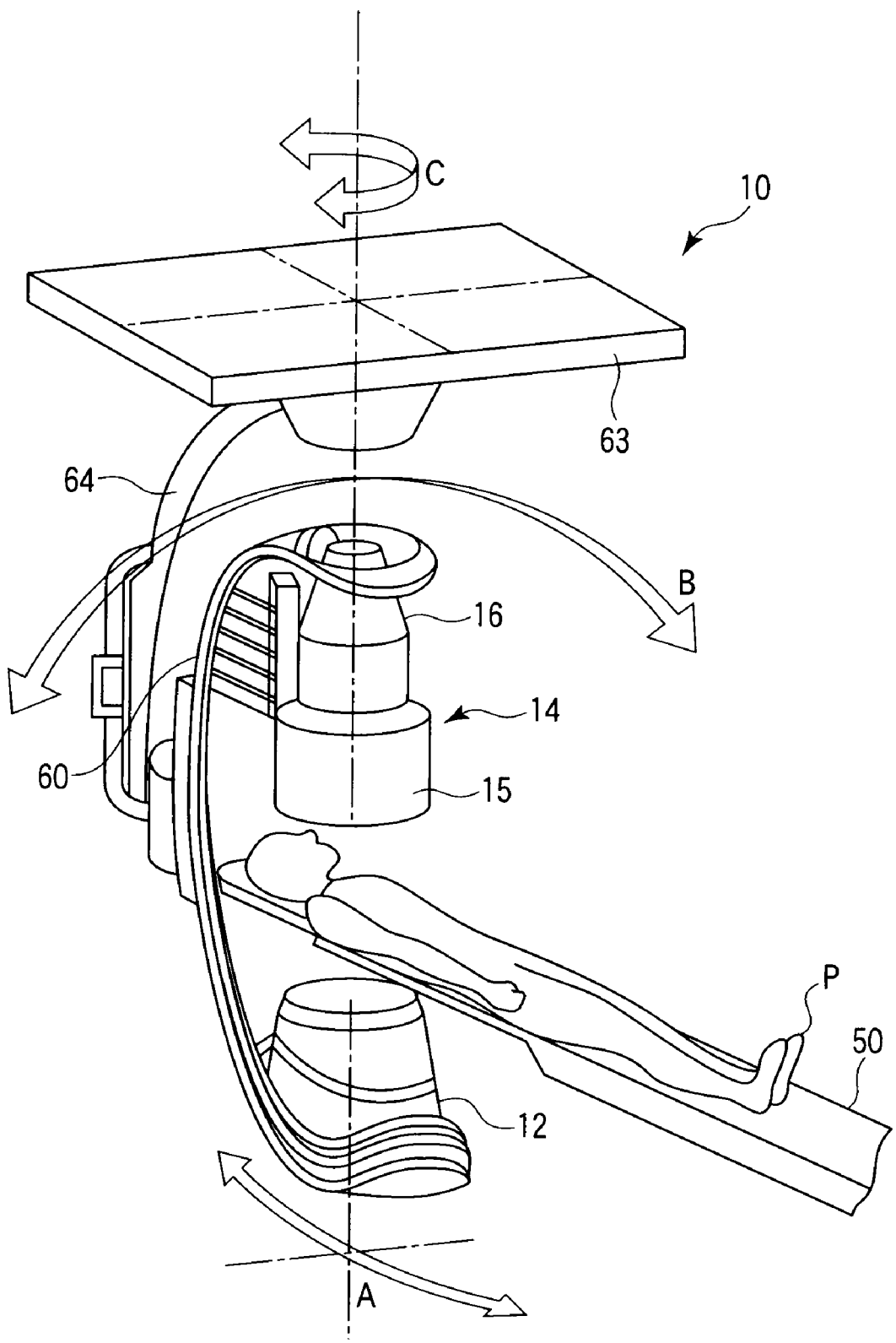
F I G. 2

X-RAY IMAGING APPARATUS

CROSS-REFERENCE TO RELATED APPLICATIONS

This application is based upon and claims the benefit of priority from prior Japanese Patent Application No. 2007-187426, filed Jul. 18, 2007, the entire contents of which are incorporated herein by reference.

BACKGROUND OF THE INVENTION

1. Field of the Invention

The present invention relates to an X-ray imaging apparatus which generates a three-dimensional image of a blood vessel from images before and after the injection of a contrast medium.

2. Description of the Related Art

There is an examination technique called CTHA (CT during hepatic arteriography) for diagnosing a liver tumor. This is a method of performing CT (Computed Tomography) of a hepatic artery while injecting a contrast medium into it. In general, however, this technique can be implemented by only an apparatus (called an IVR-CT) comprising both a CT apparatus and an angiography apparatus. An IVR-CT is very expensive, and hence only some large hospitals can purchase it.

Recently, there has been proposed a method (to be referred to as soft tissue imaging hereinafter) of improving the visibility of a soft tissue by acquiring many projection images using an X-ray imaging apparatus and reconstructing an image from the many projection images.

It is expected that if soft tissue imaging can do the same thing as CTHA, even hospitals which do not own IVR-CTs can perform the same examination as that described above. On the other hand, even if soft tissue imaging can perform the same examination as that by CTHA, conventional 3D-DSA is an indispensable examination for identifying a nutrition blood vessel and an approach route.

CTHA as soft tissue imaging is, however, inferior to CT in density resolution, and hence requires a larger amount of contrast medium. It is therefore feared that an increasing amount of contrast medium will increase the burden on a patient. See Jpn. Pat. Appln. KOKAI Publication No. 2007-130244.

BRIEF SUMMARY OF THE INVENTION

It is an object of the present invention to provide an X-ray imaging apparatus which can generate two types of three-dimensional images by one rotation radiography.

According to an aspect of the present invention, there is provided an X-ray imaging apparatus comprising a substantially C-arm, a support mechanism which rotatably supports substantially the C-arm, a rotation driving unit which drives rotation of substantially the C-arm, an X-ray tube mounted on substantially the C-arm, an X-ray detector mounted on substantially the C-arm, and a control unit which controls at least one of the rotation driving unit and an imaging control unit to make intervals between a plurality of contrast-enhanced images shorter than intervals between a plurality of mask images by changing a rotational speed of substantially the C-arm before and after injection of a contrast medium.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out herein after.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 2 is a perspective view showing the outer appearance of an X-ray imaging mechanism in FIG. 1;

DETAILED DESCRIPTION OF THE INVENTION

An X-ray imaging apparatus according to a preferred embodiment of the present invention will be described below with reference to the views of the accompanying drawing.

Figure 1:
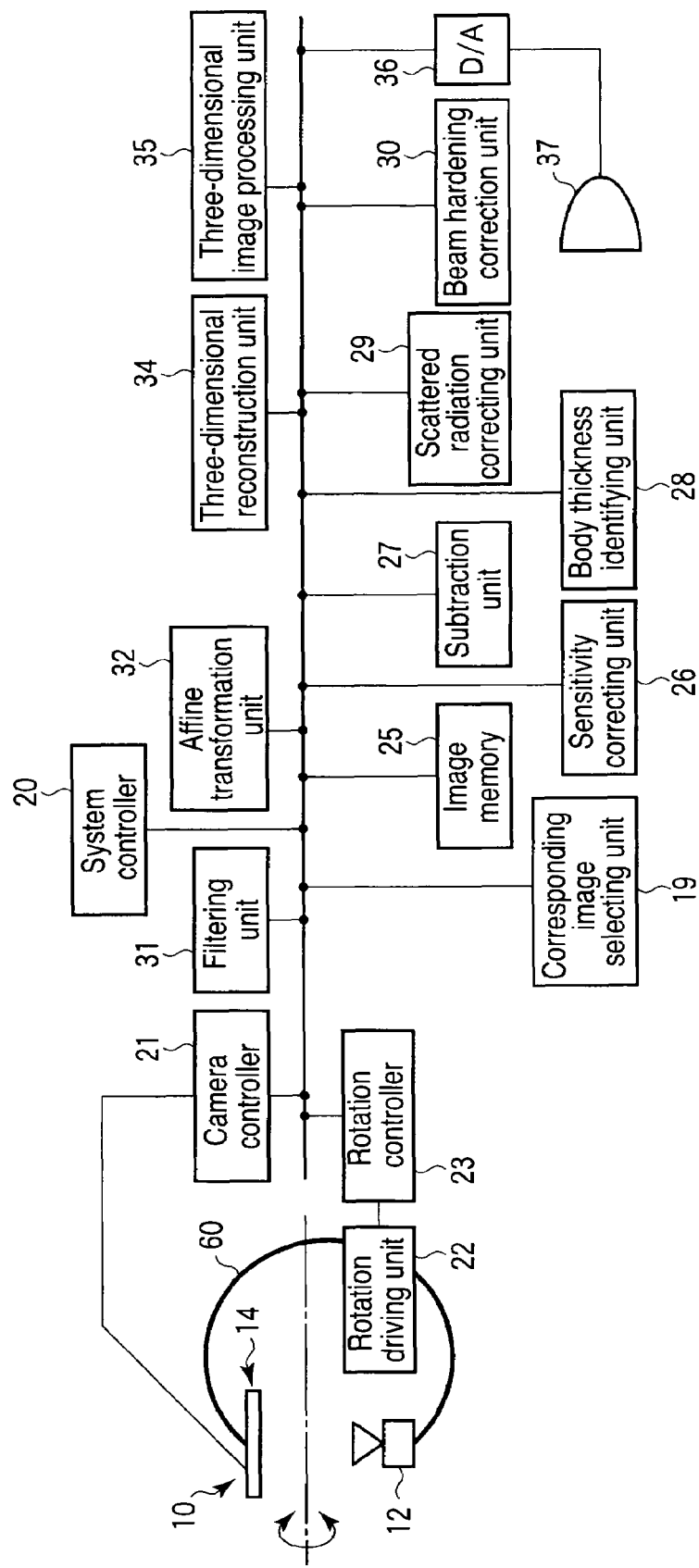
FIG. 1 is a block diagram showing the arrangement of an X-ray imaging apparatus according to an embodiment.

As shown in FIG. 1, the X-ray imaging apparatus includes an X-ray imaging mechanism 10. As shown in FIG. 2, the X-ray imaging mechanism 10 includes an X-ray tube 12 and an X-ray detector 14. The X-ray detector 14 comprises an image intensifier 15 and a TV camera 16. Alternatively, the X-ray detector 14 comprises a flat panel detector (FPD) having semiconductor detection elements arrayed in a matrix form. The X-ray tube 12 and the X-ray detector 14 are mounted on a C-arm 60 so as to face each other. A subject P on a top 50 of a bed is placed between the X-ray tube 12 and the X-ray detector 14. The C-arm 60 is supported by a column 64 suspended from a ceiling base 63 or by a floor-type stand. The C-arm 60 is rotatable with respect to three orthogonal axes A, B, and C. A rotation driving unit 22 is housed in the column 64. The rotation driving unit 22 includes two power sources for separately rotating the C-arm 60 in the directions indicated by arrows A and B. The rotation driving unit 22 can rotate the C-arm 60 at a high speed like a propeller.

In addition to the X-ray imaging mechanism 10, the X-ray imaging apparatus includes a system controller 20, a camera controller 21, a rotation controller 23, an image memory 25, a sensitivity correcting unit 26, a corresponding image selecting unit 19, a subtraction unit 27, a body thickness identifying unit 28, a scattered radiation correcting unit 29, a beam hardening correction unit 30, a filtering unit 31 which performs harmonic enhancement filtering or the like, an affine transformation unit 32 which performs image enlarge/movement and the like, a three-dimensional reconstruction unit 34, a three-dimensional image processing unit 35, a D/A conversion unit 36, and a display unit 37.

While rotating the C-arm 60 at a high speed like a propeller using the rotation driving unit 22, as described above, and changing the projection angle, the apparatus repeats radiography at intervals of, for example, 1° and acquires obtained X-ray intensity distributions (X-ray images) of 200 patterns corresponding to a rotation angle, for example, 200°. After a contrast medium is injected, the apparatus repeats radiography at intervals of, for example, 0.5° while rotating the C-arm 60 and changing the projection angle in the same manner as described above, and acquires obtained X-ray intensity distributions (X-ray images) of 400 patterns corresponding to a rotation angle, for example, 200°. The analog/digital converter (A/D converter) in the camera controller 21 converts the projected X-ray images into digital signal. Note that the X-ray images generated before the contrast medium is injected or before the contrast medium flows into a radiography region are called mask images, and the X-ray images generated after the contrast medium is injected or after the contrast medium flows into the radiography region are called contrast-enhanced images.

The image memory 25 is provided to store data associated with a plurality of mask images obtained by radiography before the injection of a contrast medium and data associated with a plurality of contrast-enhanced images obtained by radiography after the injection of the contrast medium. The corresponding image selecting unit 19 selects contrast-enhanced images after the injection of the contrast medium which match, in radiographic angle, the plurality of mask images obtained by radiography before the injection of the contrast medium. That is, the corresponding image selecting unit 19 identifies a plurality of contrast-enhanced images after the injection of the contrast medium which are obtained at radiographic angles equal to or closest to those of the plurality of mask images obtained by radiography before the injection of the contrast medium. The subtraction unit 27 generates a plurality of difference images (DSA (Digital Subtraction Angiography) images) which differ in radiographic angle by subtracting the plurality of mask images and the plurality of contrast-enhanced images selected by the corresponding image selecting unit 19, which are equal or closest to each other in terms of radiographic angle.

The three-dimensional reconstruction unit 34 reconstructs a three-dimensional image (first three-dimensional image) on the basis of a plurality of difference images.

That is, the three-dimensional reconstruction unit 34 reconstructs a first three-dimensional image on the basis of the difference images based on a plurality of mask images and some of a plurality of contrast-enhanced images.

The three-dimensional image processing unit 35 converts the reconstructed first three-dimensional image into a three-dimensional image by, for example, volume rendering or the like. This image is a three-dimensional blood vessel image (3D-DSA image) having only information about blood vessels. The filtered backprojection method proposed by Feldkamp et al. will be described as an example of the reconstruction methods. A proper convolution filter like a Shepp & Logan filter or a Ramachandran filter is applied to the DSA images of 200 frames. This method then obtains reconstruction data by performing backprojection computation. In this case, a reconstruction region is defined as a cylinder inscribed in a bundle of X-rays in all direction of the X-ray tube 12. For example, the interior of this cylinder must be three-dimensionally discretized with a length d of the central portion of the reconstruction region projected by the width of one detection element of the X-ray detector 14, and a reconstructed image of data of the discrete points must be obtained. In this case, the discretization interval is an example. Since various techniques are available, the discretization interval defined by the apparatus may be basically used.

The three-dimensional reconstruction unit 34 reconstructs a three-dimensional image (second three-dimensional image) on the basis of all the generated contrast-enhanced images. This three-dimensional image corresponds to a so-called CTHA image (soft tissue image) which improves the visibility of the soft tissue. The details of this image will be described later.

The greatest advantage of this embodiment is that the operation of generating contrast-enhanced images can be made common to radiographing operation for 3D-DSA and radiographing operation for CT-like imaging. That is, this embodiment generates mask images and contrast-enhanced images in radiographing operation for 3D-DSA, and executes CT-like imaging using the contrast-enhanced images. In other words, the embodiment generates contrast-enhanced images in radiographing operation for CT-like imaging, but executes 3D-DSA using several images of the contrast-enhanced images and the mask images generated in 3D-DSA radiographing operation. Note that CT-like imaging requires a larger number of contrast-enhanced images than 3D-DSA. In addition, the intervals between the images are shorter.

Figure 3:
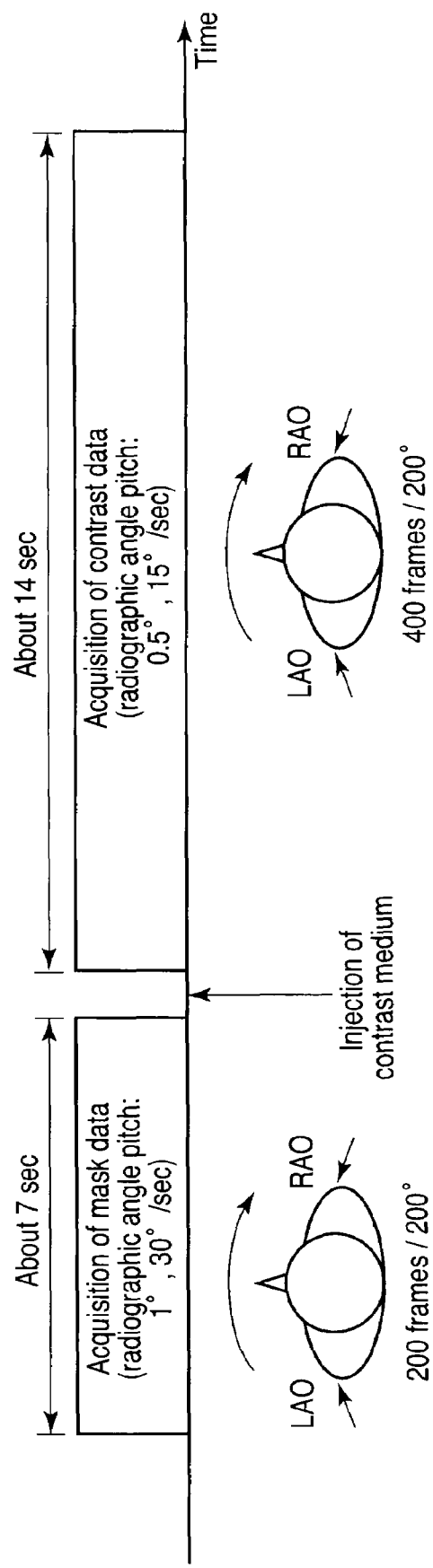
FIG. 3 is a view showing a radiography sequence in this embodiment.

As shown in FIG. 3, the acquisition of projection data is performed twice before and after the injection of a contrast medium. In radiography before the injection of a contrast medium, the apparatus repeats radiographing operation at a predetermined frame rate, typically 30 fps, while rotating the C-arm 60 at, for example, a rate of 30°/sec. With this operation, mask images of 200 frames are acquired at intervals of 1°. The analog/digital converter in the camera controller 21 converts the data of the acquired mask images of 200 frames into digital signals, and stores the signals in the image memory 25 in correspondence with the respective radiographic angle data. Thereafter, the C-arm 60 is returned to the initial rotation start position. A contrast medium is then injected with a contrast medium injector, and the apparatus repeats radiography at the same frame rate (30 fps) while rotating the C-arm 60 at a rate of 15°/sec, which is ½ the rate in radiography before the injection of the contrast medium. With this operation, contrast-enhanced images are acquired at intervals of 0.5°, which is ½ the intervals in radiography before the injection of the contrast medium. The data of the acquired contrast-enhanced images of 400 frames are stored in the image memory 25.

Note that if the read rate (frame rate) of the X-ray detector 14 can be increased, it suffices to adjust the rotational speed of the C-arm 60 to 30°/sec and the image read rate of the detector to 60 frames/sec. The data of the contrast-enhanced images of 400 frames are stored in the image memory 25 in correspondence with the respective radiographic angle data.

The number of contrast-enhanced images is almost two times, three times, or four times that of mask images.

Figure 4:
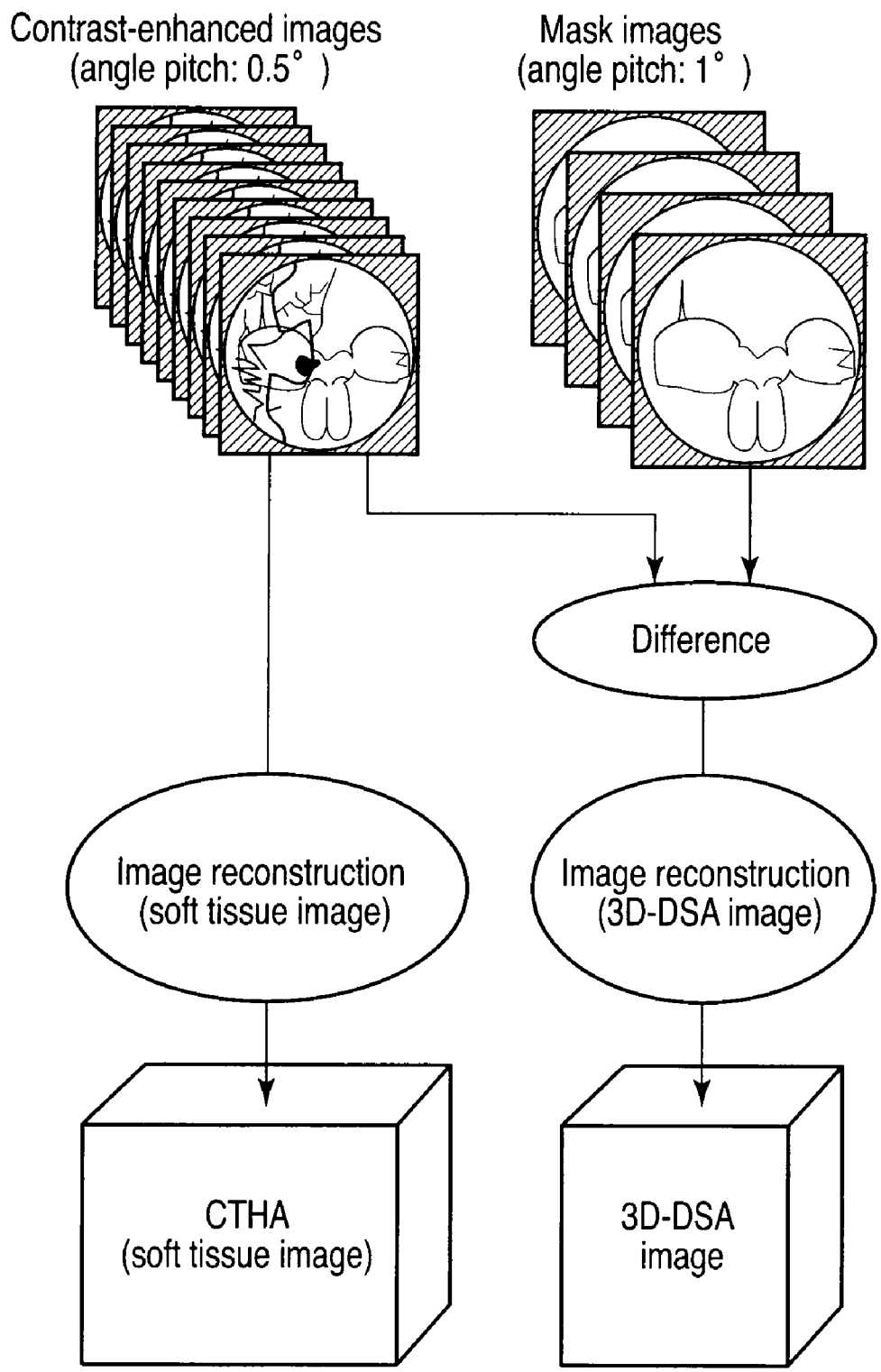
FIG. 4 is a view showing an image processing sequence in this embodiment.

As shown in FIG. 4, after the radiography, for the 200 mask images ($IM_N$), the corresponding image selecting unit 19 selects 200 contrast-enhanced images ($IC_n$), from the 400 contrast-enhanced images, which are equal in radiographic angle to the mask images. The 200 contrast-enhanced images ($IC_N$) and the 200 mask images ($IM_n$) which are equal in radiographic angle are subtracted from each other. The three-dimensional reconstruction unit 34 reconstructs a first three-dimensional image (3D-DSA image) on the basis of the 200 difference images. This three-dimensional image mainly represents a blood vessel form as a contrast-enhanced region, with a non-blood vessel region such as a bone and soft tissue which are not contrast-enhanced being mainly removed. The reconstructed image is transferred to the three-dimensional image processing unit 35. The three-dimensional image processing unit 35 then converts the image into a three-dimensional image by volume rendering or the like, and displays it on the display unit 37 via the D/A conversion unit 36.

This apparatus generates a CTHA image (second three-dimensional image) concurrently with or before or after the generation of this three-dimensional image and display processing. A CTHA image is generated by using all the acquired 400 contrast-enhanced images ($IC_n$). First of all, the sensitivity correcting unit 26 subtracts the contrast-enhanced images and images for detector sensitivity correction. The images for detector sensitivity correction are data representing the sensitivity of the detector and X-ray intensity differences. The sensitivity correcting unit 26 subtracts the contrast-enhanced images after the injection of the contrast medium from the images for detector sensitivity correction. The three-dimensional reconstruction unit 34 reconstructs a three-dimensional image from a plurality of sensitivity-corrected contrast-enhanced images. The body thickness identifying unit 28 performs threshold processing for this three-dimensional image to separate the image into a born portion, a soft tissue portion, and a background region. The apparatus then generates projection images of 400 frames by projecting this three-dimensional image in the same directions as those in the radiography. The apparatus calculates thicknesses $B(\theta, i, j)$ and $T(\theta, i, j)$ of a bone and soft tissue on an X-ray path for each pixel of each projection image.

The thickness data $B(\theta, i, j)$ and $T(\theta, i, j)$ and projection data $P(\theta, i, j)$ are sent to the scattered radiation correcting unit 29. Scattered radiation correction is performed by using the thicknesses of the bone and soft tissue and referring to a two-dimensional correction table. The beam hardening correction unit 30 then corrects the values of the projection images by also referring to the two-dimensional correction table on the basis of the thickness data. Note that the correction table is empirically obtained.

The projection images of 400 frames having undergone the scattered radiation correction and beam hardening correction are sent to the three-dimensional reconstruction unit 34 to be used for the reconstruction of a third three-dimensional image. This three-dimensional image is an image approximate to a CTHA image. Obtaining a CTHA image as an image obtained by soft tissue imaging and a 3D-DSA image by one radiography in this manner makes it possible to reduce the dose to the patient and the amount of contrast medium used and shorten the examination time, thereby reducing the burden on the patient.

This embodiment has exemplified the method of changing an angle sampling pitch by changing a rotational speed while fixing a frame rate. In the embodiment, the rotational speed in radiography for mask images is different from that in radiography for contrast-enhanced images, and hence the vibrations of the C-arm and the like vary. In the strict sense, therefore, correction data for vibrations and the like must be measured separately in advance. If, however, the frame rate can be increased, it suffices to change the angle sampling pitch by changing the frame rate while fixing the rotational speed. In the embodiment, correction data can be commonly used for the acquisition of mask images and for the acquisition of contrast-enhanced images.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An X-ray imaging apparatus comprising:
   a substantially C-arm;
   a support mechanism which rotatably supports the substantially C-arm;
   a rotation driving unit which drives rotation of the substantially C-arm;
   an X-ray tube mounted on the substantially C-arm;
   an X-ray detector mounted on the substantially C-arm; and
   a control unit which controls the rotation driving unit to make intervals between a plurality of contrast-enhanced images shorter than intervals between a plurality of mask images by changing a rotational speed of the substantially C-arm before and after injection of a contrast medium.

2. The apparatus according to claim 1, further comprising:
   a difference processing unit which generates a plurality of difference images from the plurality of mask images and several images of the plurality of contrast-enhanced images which match, in radiographic angle, the plurality of mask images; and
   a reconstruction unit which reconstructs a first three-dimensional image on the basis of the plurality of difference images, and a second three-dimensional image on the basis of the plurality of contrast-enhanced images.

3. The apparatus according to claim 1, wherein the intervals between the contrast-enhanced images are substantially ½ or less than ½ the intervals between the mask images.

4. The apparatus according to claim 3, wherein the intervals between the contrast-enhanced images are 0.5°.

5. The apparatus according to claim 1, wherein the number of contrast-enhanced images obtained by radiography is substantially two times, substantially three times, or substantially four times the number of times of radiography for the mask images.

6. The apparatus according to claim 1, wherein the contrast-enhanced images are 400 frames, and the mask images are 200 frames or 100 frames.

7. An X-ray imaging apparatus comprising:
   a substantially C-arm;
   a support mechanism which rotatably supports the substantially C-arm;
   a rotation driving unit which drives rotation of the substantially C-arm;
   an X-ray tube mounted on the substantially C-arm;
   an X-ray detector mounted on the substantially C-arm; and
   a control unit which controls the X-ray detector to make intervals between a plurality of contrast-enhanced images shorter than intervals between a plurality of mask images by changing an acquisition rate of the X-ray detector before and after injection of a contrast medium.

8. The apparatus according to claim 7, further comprising:
   a difference processing unit which generates a 0plurality of difference images from the plurality of mask images and several images of the plurality of contrast-enhanced images which match, in radiographic angle, the plurality of mask images; and
   a reconstruction unit which reconstructs a first three-dimensional image on the basis of the plurality of difference images, and a second three-dimensional image on the basis of the plurality of contrast-enhanced images.

9. The apparatus according to claim 7, wherein the intervals between the contrast-enhanced images are substantially ½ or less than ½ the intervals between the mask images.

10. The apparatus according to claim 9, wherein the intervals between the contrast-enhanced images are 0.5°.

11. The apparatus according to claim 7, wherein the number of contrast-enhanced images obtained by radiography is substantially two times or substantially four times the number of times of radiography for the mask images.

12. The apparatus according to claim 7, wherein the contrast-enhanced images are 400 frames, and the mask images are 200 frames or 100 frames.

13. An X-ray imaging apparatus comprising:
    a substantially C-arm;
    a support mechanism which rotatably supports the substantially C-arm;

a rotation driving unit which drives rotation of the substantially C-arm;

an X-ray tube mounted on the substantially C-arm;

an X-ray detector mounted on the substantially C-arm; and a control unit which controls the rotation driving unit and the X-ray detector to make intervals between a plurality of contrast-enhanced images shorter than intervals between a plurality of mask images.

14. The apparatus according to claim 13, further comprising:

a difference processing unit which generates a plurality of difference images from the plurality of mask images and several images of the plurality of contrast-enhanced images which match, in radiographic angle, the plurality of mask images; and a reconstruction unit which reconstructs a first three-dimensional image on the basis of the plurality of difference images, and a second three-dimensional image on the basis of the plurality of contrast-enhanced images.

15. The apparatus according to claim 13, wherein the intervals between the contrast-enhanced images are substantially ½ or less than ½ the intervals between the mask images.

16. The apparatus according to claim 15, wherein the intervals between the contrast-enhanced images are 0.5°.

17. The apparatus according to claim 13, wherein the number of contrast-enhanced images obtained by radiography is substantially two times, substantially three times, or substantially four times the number of times of radiography for the mask images.

18. The apparatus according to claim 13, wherein the contrast-enhanced images are 400 frames, and the mask images are 200 frames or 100 frames.

19. An X-ray imaging apparatus comprising:

a substantially C-arm;

a support mechanism which rotatably supports the substantially C-arm;

a rotation driving unit which drives rotation of the substantially C-arm;

an X-ray tube mounted on the substantially C-arm;

an X-ray detector mounted on the substantially C-arm;

a control unit which controls the rotation driving unit and the X-ray detector to generate a plurality of mask images and a plurality of contrast-enhanced images before and after injection of a contrast medium; and a reconstruction unit which reconstructs a first three-dimensional image on the basis of difference images based on the plurality of mask images and several images of the plurality of contrast-enhanced images, and reconstructs a second three-dimensional on the basis of the plurality of contrast-enhanced images.

20. The apparatus according to claim 19, wherein the number of contrast-enhanced images obtained by radiography is substantially two times, substantially three times, or substantially four times the number of times of radiography for the mask images.

* * * * *